(12) United States Patent
Mann

(10) Patent No.: US 10,408,765 B2
(45) Date of Patent: Sep. 10, 2019

(54) MAGNIFYING IMAGING OPTICAL UNIT AND EUV MASK INSPECTION SYSTEM WITH SUCH AN IMAGING OPTICAL UNIT

(71) Applicant: Carl Zeiss SMT GmbH, Oberkochen (DE)

(72) Inventor: Hans-Juergen Mann, Oberkochen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 901 days.

(21) Appl. No.: 14/835,308

(22) Filed: Aug. 25, 2015

(65) Prior Publication Data

US 2015/0362438 A1    Dec. 17, 2015

Related U.S. Application Data

(63) Continuation of application No. PCT/EP2014/054414, filed on Mar. 7, 2014.
(Continued)

(30) Foreign Application Priority Data

Mar. 14, 2013   (DE) .................. 10 2013 204 445

(51) Int. Cl.
| | | |
|---|---|---|
| *G01N 21/88* | (2006.01) | |
| *G02B 17/06* | (2006.01) | |
| *G01N 21/95* | (2006.01) | |

(52) U.S. Cl.
CPC ......... *G01N 21/8806* (2013.01); *G01N 21/95* (2013.01); *G02B 17/0605* (2013.01);
(Continued)

(58) Field of Classification Search
CPC .... G01N 21/00; G01N 21/88; G01N 21/8806; G01N 21/95; G02B 17/08;
(Continued)

(56) References Cited

U.S. PATENT DOCUMENTS

| | | |
|---|---|---|
| 4,812,030 A | 3/1989 | Pinson |
| 4,863,253 A | 9/1989 | Shafer et al. |

(Continued)

FOREIGN PATENT DOCUMENTS

| | | |
|---|---|---|
| CN | 201166733 | 12/2008 |
| DE | 697 31 691 T2 | 12/2005 |
| WO | WO 2012/101269 A1 | 8/2012 |

OTHER PUBLICATIONS

Pdf of "https://www.opto-e.com/resources/telecentric-lenses-tutorial" (Year: 2015).*
(Continued)

*Primary Examiner* — Robert E. Tallman
(74) *Attorney, Agent, or Firm* — Fish & Richardson P.C.

(57) ABSTRACT

A magnifying imaging optical unit serves for inspecting lithography masks which are used in EUV projection exposure. The imaging optical unit comprises at least two mirrors (M1 to M4) which can be displaced relative to one another for changing a magnification value. According to a further aspect, a magnifying imaging optical unit comprises at least one mirror (M1 to M4) and a magnification value, which can be changed by displacement of at least two mirrors (M1 to M4) relative to one another. Here, the magnification value can be changed between a minimum magnification value, which is greater than 100, and a maximum magnification value, which is greater than 200. An imaging optical unit emerges, which can be adapted to, in particular, mask structures with different sizes.

20 Claims, 5 Drawing Sheets

Related U.S. Application Data

(60) Provisional application No. 61/782,167, filed on Mar. 14, 2013.

(52) U.S. Cl.
CPC ..... G02B 17/0657 (2013.01); G02B 17/0663 (2013.01); G02B 17/0694 (2013.01); *G01N 2201/068* (2013.01); *G01N 2201/06113* (2013.01)

(58) Field of Classification Search
CPC .............. G02B 17/0804; G02B 17/082; G02B 17/0836; G02B 17/0856; G02B 17/0884; G02B 17/0892; G02B 17/0896; G02B 21/00; G02B 21/0004; G02B 21/0016; G02B 21/002; G02B 21/0024; G02B 21/0028; G02B 21/0032
USPC ....... 359/362, 368, 371, 372, 379, 380, 382, 359/383, 385, 386, 389
See application file for complete search history.

(56) References Cited

U.S. PATENT DOCUMENTS

| | | | |
|---|---|---|---|
| 4,964,706 A | 10/1990 | Cook | |
| 5,144,476 A * | 9/1992 | Kebo | G02B 15/00 359/366 |
| 5,410,434 A | 4/1995 | Shafer | |
| 6,333,811 B1 * | 12/2001 | Tatian | G02B 15/14 359/365 |
| 7,130,018 B2 * | 10/2006 | Terasawa | G02B 17/0657 355/53 |
| 7,623,620 B2 * | 11/2009 | Mann | G21K 7/00 359/368 |
| 2005/0036219 A1 | 2/2005 | Doittau et al. | |
| 2007/0035814 A1 * | 2/2007 | Dinger | B82Y 10/00 359/350 |
| 2008/0175349 A1 * | 7/2008 | McGuire | G03F 7/70291 378/34 |
| 2008/0285713 A1 * | 11/2008 | Hayashi | G03F 7/70841 378/34 |
| 2011/0242528 A1 | 10/2011 | Hwang et al. | |
| 2012/0140454 A1 | 6/2012 | Mann | |

OTHER PUBLICATIONS

German Office Action, with translation thereof, for corresponding DE Appl. No. 10 2013 204 445.3, dated Jun. 10, 2013.
Chinese office action and search report, with English translation, for corresponding Appl No. 2014 8001 4299, dated Apr. 20, 2017.
International Search Report for corresponding International Patent Appln No. PCT/EP2014/054414 dated Jun. 18, 2014.
Chinese office action, with English translation thereof, for corresponding CN Appl No. 2014 8001 4299.4, dated Apr. 4, 2018.
Japanese Office Action for U.S. Appl. No. JP 2015-562032 (with English translation), dated Jan. 19, 2018, 6 pages.

\* cited by examiner

MAGNIFYING IMAGING OPTICAL UNIT AND EUV MASK INSPECTION SYSTEM WITH SUCH AN IMAGING OPTICAL UNIT

CROSS-REFERENCE TO RELATED APPLICATIONS

The present application is a continuation of, and claims benefit under 35 USC 120 to, international application of PCT/EP2014/054414, filed Mar. 7, 2014, which claims benefit under 35 USC 119 of German Application No. 10 2013 204 445.3, filed Mar. 14, 2013. International application of PCT/EP2014/054414 also claims priority under 35 USC 119(e) to U.S. Provisional Application No. 61/782,167, filed Mar. 14, 2013. The contents of international application of PCT/EP2014/054414 and German patent application 10 2013 204 445.3 are incorporated by reference.

The invention relates to a magnifying imaging optical unit for inspecting lithography masks which are used in EUV projection exposure, and an EUV mask inspection system with such an imaging optical unit.

A magnifying imaging optical unit of the type set forth at the outset is known from WO 2012/101 269 A1 and US 2012/0140454 A1. Furthermore, imaging optical units are known from US 2011/0242528 A1, U.S. Pat. Nos. 4,863,253, 4,964,706, 5,144,476 and 6,333,811 B1.

It is an object of the present invention to develop an imaging optical unit of the type set forth at the outset in such a way that the optical unit can be adapted to, in particular, mask structures with different sizes.

According to the invention, this object is achieved by magnifying imaging optical unit for inspecting lithography masks according to a first aspect and by magnifying imaging optical unit according to a further aspect. In the first aspect, the magnifying imaging optical unit comprises at least two mirrors which can be displaced relative to one another for changing a magnification value, wherein an image field of the magnifying imaging optical unit is independent of the magnification value in terms of the size and position of the image field, and a distance between an object field and the mirrors is finite. In the second aspect, the magnifying imaging optical unit comprises at least one mirror, wherein the magnifying imaging optical unit has a magnification value which can be changed between a minimum magnification value, which is greater than 100, and a maximum magnification value, which is greater than 200, by the displacement of at least two mirrors of the magnifying imaging optical unit relative to one another.

By changing the magnification value, it is possible to ensure an adaptation of the magnifying imaging optical unit to the required structure resolution and/or the desired functionality.

The imaging optical unit according to the first aspect allows imaging of mask structures with different sizes, wherein no compromise needs to be made in respect of, firstly, the parameter resolution and, secondly, the object field size. The magnifying imaging optical unit has at least two mirrors that are displaceable relative to one another, i.e. it has at least one displaceable mirror which, for example, can be displaced with respect to at least one stationary mirror. This imaging optical unit dispenses with the necessity of adapting a position or an embodiment of an image field detection to a respective sum-position of the imaging optical unit. The distance between the object field and the mirrors of the magnifying imaging optical unit is finite and is, in particular, less than 10 m, less than 8 m, less than 6 m, less than 4 m, less than 2 m and can be less than 1 m. The distance between the object field and the mirrors can be less than 750 mm, can be less than 600 mm, can be less than 500 mm, can be less than 400 mm and can be less than 300 mm. Here, the distance value specifies the distance between the object field and the mirror lying closest thereto. The distance also can be less than 200 mm.

A micro zoom system, i.e. an imaging optical unit in which the magnification value can be changed over a broad range between in each case very large magnification values, emerges according to the second aspect. Here, the minimum magnification value can be greater than 150, can be greater than 200, can be greater than 250, can be greater than 300, can be greater than 350, can be greater than 400, can be greater than 450 and can equal 487.5. The maximum magnification value can be greater than 250, can be greater than 300, can be greater than 350, can be greater than 400, can be greater than 450, can be greater than 500, can be greater than 550, can be greater than 600, can be greater than 650, can be greater than 700, can be greater than 750, and can equal 780. A zoom factor, i.e. the ratio between the maximum magnification value and the minimum magnification value, can be greater than 1.1, can lie in the range between 1.1 and 2, between 1.2 and 1.9 or between 1.4 and 1.8 and can lie at, in particular, 1.6.

In an embodiment, the magnifying imaging optical unit includes precisely one displaceable mirror for changing the magnification value. In such an embodiment, a zoom behavior which is controllable in a particularly simple manner emerges. The production outlay for the zoom optical unit is low. In an alternative embodiment of the imaging optical unit, the latter has precisely two displaceable mirrors for changing the magnification value.

All mirrors of the imaging optical unit can have a displaceable embodiment for changing the magnification value. In such embodiments, the imaging optical unit can be adapted very finely to the respective magnification value.

An image field of the magnifying imaging optical unit can be independent of the magnification value in terms of the size and position of the image field. In such an imaging optical unit, the necessity of adapting the position or embodiment of an image field detection to the respective zoom setting of the imaging optical unit is dispensed with.

Individual features of the two aspects explained above can also be a subject matter of the invention in other combinations.

An aperture stop in the imaging beam path can be between an object field and a first mirror. The position of an aperture stop in such an embodiment is independent of a zoom setting of the magnifying imaging optical unit. A diameter and/or a lateral position of the aperture stop can be different depending on the respectively selected zoom setting and/or depending on the respectively selected functionality of the imaging optical unit. By way of example, the diameter and/or the lateral position of the aperture stop can depend on whether the imaging optical unit is used in an aerial image metrology system or in an actinic pattern mask inspection.

An intermediate image can be in the imaging beam path between an object field and an image field, wherein the intermediate image is arranged in the imaging beam path between a first mirror and a second mirror of the magnifying imaging optical unit. Such an intermediate image was found to be particularly suitable for compact beam guidance.

A catoptric embodiment magnifying imaging optical unit is particularly suitable for use with EUV wavelengths. The imaging optical unit can have precisely four mirrors. The imaging optical unit can be a coaxial system. The imaging optical unit can have an off-axis object field and/or an off-axis image field.

In some embodiments, none of the mirrors has a central passage opening for the passage of imaging light. Such embodiments of the imaging optical unit can be uncomplicated to produce.

An object-side numerical aperture can be changed between a minimum object-side numerical aperture in the range between 0.1 and 0.15 and a maximum object-side numerical aperture in the range between 0.15 and 0.25 by displacing two mirrors of the magnifying imaging optical unit with respect to one another. Such a changeable object-side numerical aperture has advantages which were already explained above in conjunction with the change in magnification value. The minimum object-side numerical aperture can be 0.125 and the maximum object-side numerical aperture can be 0.2. The image-side numerical aperture can be independent of a displacement of optical components of the imaging optical unit.

An EUV mask inspection system can comprise an imaging optical unit described above and a spatially resolving detector which detects the image field. The advantages of such an inspection or metrology system correspond to those which were already explained above with reference to the imaging optical unit. A CCD sensor can be provided as detection device. Depending on e.g. a scanning operation of the system, a TDI (time-delayed integration) sensor may also be used as detection device.

An EUV mask inspection system can comprise an EUV light source. Such an EUV light source can be a plasma source, a synchrotron source or else e.g. a free electron laser (FEL). The EUV light source can produce imaging light with a wavelength in the range between 5 nm and 30 nm. Exemplary embodiments of the invention will be explained in more detail below on the basis of the drawing. In detail:

FIG. 1 schematically shows an inspection or metrology system for examining objects, wherein a reflecting reticle for EUV projection lithography serves as object to be examined;

FIG. 2 shows a further embodiment of an inspection or metrology system in a similar illustration to FIG. 1, wherein a transmissive reticle for EUV projection lithography, e.g. a phase shift mask, serves as object to be examined;

FIG. 3 shows a meridional section through an embodiment of a magnifying imaging zoom optical unit for use in an inspection or metrology system according to FIG. 1 or 2, wherein the imaging optical unit serves to simulate and analyze effects and properties of lithography masks, i.e. reticles, on an optical imaging within a projection optical unit of a projection exposure apparatus for EUV projection lithography or else for large-area detection of mask defects;

Figure 1:
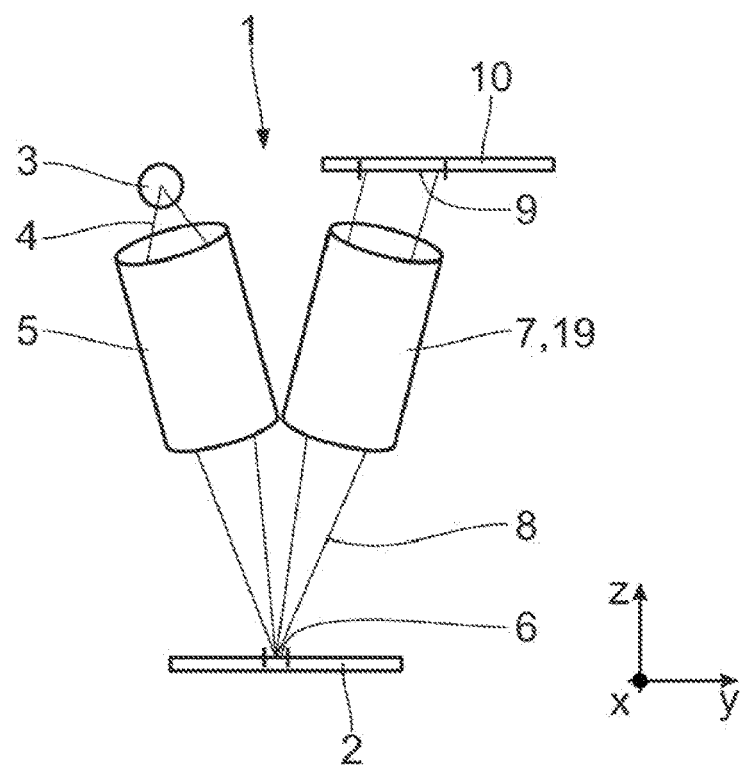

FIG. 1 shows, very schematically, an inspection or metrology system 1 for examining an object 2 in the form of a reticle or a lithography mask for EUV projection lithography. Using the metrology system 1, which is also referred to as actinic patterned mask inspection system, it is possible to examine, in particular, defects on the reticle 2 and the effects thereof on the imaging during EUV projection lithography.

In particular, the reticle 2 can be checked for structuring errors. The structuring error can subsequently be examined with the aid of an analysis of a so-called aerial image (aerial image metrology system). Such systems are known from DE 102 20 815 A1. The inspection system 1 is employed to examine a reflecting reticle 2.

The aerial image can be recorded with the aid of the same metrology system 1, in particular with the same optical unit, with which the reflecting reticle 2 is examined. Optical parameters, such as field size, stop position and zoom setting, which will in part still be explained in more detail below, are adapted in accordance with the purpose of the metrology system 1. The use of one and same metrology system 1 for aerial image analysis on the one hand and for examining the reflecting reticle 2 on the other hand avoids a reticle to be examined having to be transported from one metrology system to a further metrology system by a transport method which is complicated in respect of cleanliness requirements.

In order to simplify the illustration of positional relationships, use is made of a Cartesian xyz-coordinate system in the following text. In FIG. 1, the x-axis extends perpendicular to the plane of the drawing and out of the latter. In FIG. 1, the y-axis extends to the right. In FIG. 1, the z-axis extends upwards.

The inspection system 1 has an EUV light source 3 for producing illumination and imaging light 4. The EUV light source can be a plasma source, i.e., for example, an LPP (laser produced plasma) source or a GDP (gas discharge produced plasma) source. The EUV light source 3 can also be an EUV laser. By way of example, the latter can be realized by frequency multiplication of longer-wavelength laser radiation. The EUV light source 3 emits usable illumination and imaging light 4 with a wavelength of 13.5 nm. In the case of an appropriate configuration of the EUV light source 3, it is also possible to use other wavelengths in the range between 5 nm and 100 nm, in particular in the range between 5 nm and 30 nm, as illumination and imaging light 4.

An illumination optical unit serves for transmitting the illumination and imaging light 4 from the EUV light source 3 to an object field 6, in which a section of the reflecting reticle 2 is arranged.

An imaging optical unit 7 with a large magnification value, e.g. of 500, images the object field 6 in an image field 9 via an imaging beam path 8. A spatially resolving detection device in the form of a CCD sensor 10 detects an intensity distribution of the illumination and imaging light 4 via the image field 9. A CCD chip of the CCD sensor 10 can be embodied as time delay and integration CCD (charge coupled device) chip. In particular, such a CCD chip can be employed for examining a reticle 2 moved through the object field 6. A displacement direction of the reticle 2 can extend along the y-direction.

An illumination and a detection of the illumination and imaging light 4 emanating from the object field 6 can occur in different ways. In the case of the inspection system 1 according to FIG. 1, there is illumination with a numerical aperture NA of e.g. 0.2. Depending on the embodiment, the imaging optical unit 7 can detect this numerical aperture wholly or in part. Thus, given a perfectly reflecting reticle 2, all of the illumination and imaging light 4 reflected by the reticle 2, or part thereof, can be detected by the imaging optical unit 7. Such illumination is also known as bright field illumination. Dark field illumination is also possible; in this case, it is only in portions of the illumination and imaging light 4 that are scattered or diffracted by the reticle 2 that are detected by the CCD sensor 10.

Figure 2:
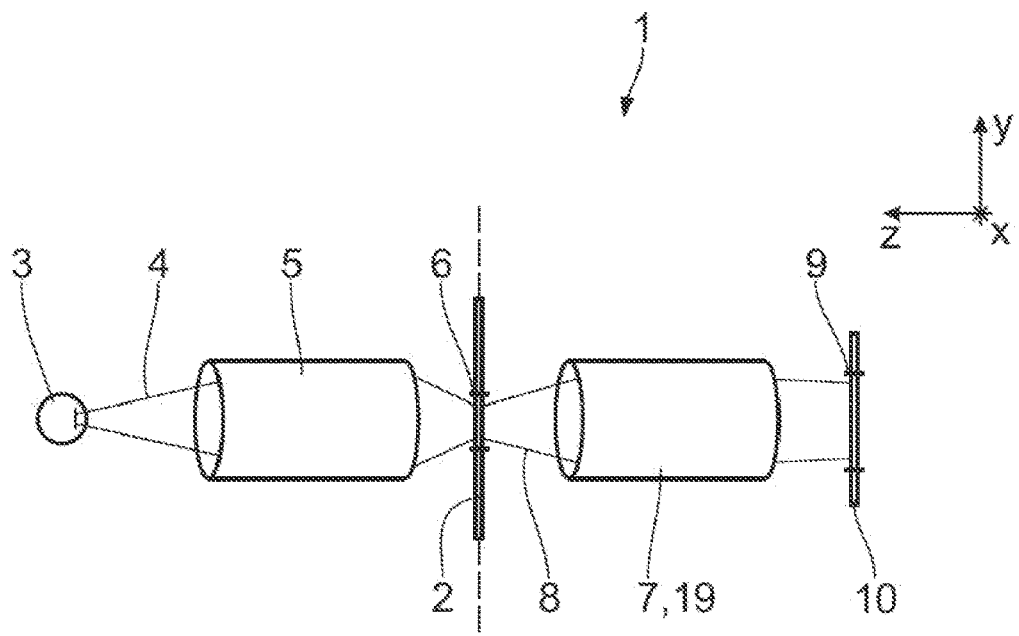

FIG. 2 shows a variant of the inspection system 1, which is employed for examining a reticle 2, e.g. a phase shift mask, through which the illumination and imaging light 4 can be transmitted, at least part. Components corresponding to those that were already explained above with reference to FIG. 1 are denoted by the same reference signs and will not once again be discussed in detail.

In contrast to the embodiment according to FIG. 1, the imaging optical unit 7 in the inspection system 1 according to FIG. 2 is not arranged in the direction of a reflected beam path of the illumination and imaging light 4, but rather in the direction of a beam path which was allowed to pass through the reticle 2. Here, a bright field illumination or a dark field illumination is also possible, depending on the embodiment of the illumination optical unit 5 and/or the imaging optical unit 7.

Figure 3:
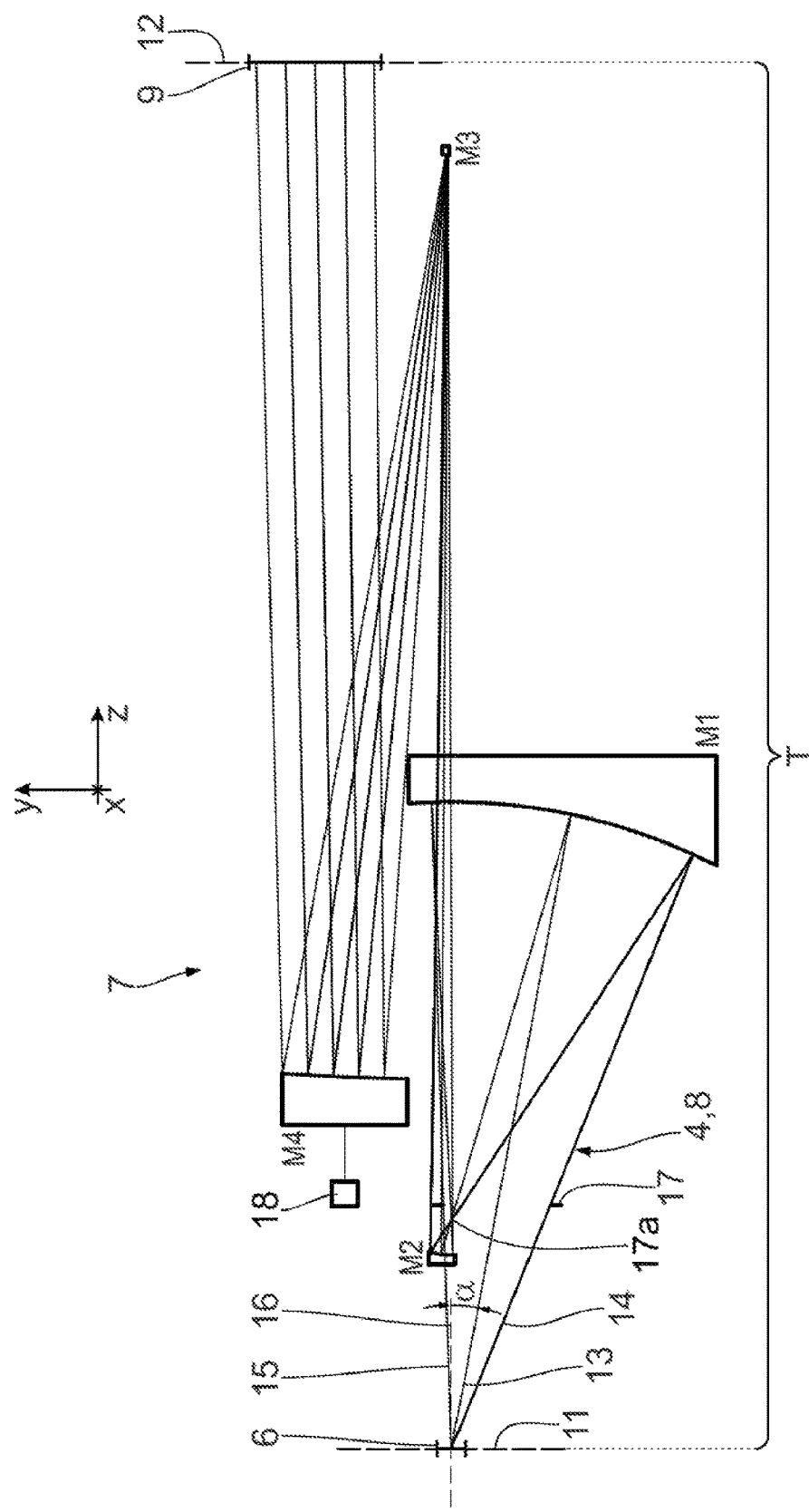

FIG. 3 shows an embodiment of the imaging optical unit 7, which can be used in the inspection system 1 according to FIG. 1 or 2. Components that were already explained above in conjunction with the description of the inspection system 1 are denoted by the same reference signs and will not once again be discussed in detail. A Cartesian xyz-coordinate system is also used in conjunction with the description of the imaging optical unit 7 according to FIG. 3 and with the description of the further embodiments. In FIG. 3, the x-axis extends perpendicular to the plane of the drawing and into the latter. In FIG. 3, the y-axis extends upwards. In FIG. 3, the z-axis extends to the right.

The imaging optical unit 7 according to FIG. 3 images the object field 6, which lies in an object plane 11, into the image field 9, which lies in an image plane 12, with a magnification value of 780.

FIG. 3 illustrates, for the visualization of the imaging beam path 8 of the imaging optical unit 7, the course of chief rays 13 and of coma rays 14, 15 which emerge from five object field points lying one above another in the y-direction. The distance between the object field points in the y-direction is so small in the object field 6 that the distance cannot be resolved in the drawing. These five object field points are imaged into five image field points lying one above another in FIG. 3 in the image field 9, which are resolved separately in the drawing on account of the high magnification factor. The chief rays 13, on the one hand, and the coma rays 14, 15, on the other hand, are also designated as imaging rays in the following text.

The object field 6, on the one hand, and the image field 9, on the other hand, lie in xy planes spaced apart from one another. The object field 6 has an extent of 153 μm in the y-direction and an extent of 204 μm in the x-direction, that is to say has a field size of 153×204 μm². The object field 6 and the image field 9 are rectangular in each case.

The chief rays 13 emerge in the imaging beam path 8 between the object field 6 and the image field 9 from the object field 6 with a chief ray angle α of approximately 10° with respect to a normal 16—extending in a z-direction—of a central object field point of the object plane 11. As a result of this large chief ray angle α, the imaging optical unit 7 according to FIG. 3 can be employed for imaging a reflecting reticle. Other chief ray angles α, in particular a smaller chief ray angles α, are possible.

An object-field side numerical aperture of the imaging optical unit 7 is NAO=0.2.

In the image plane 12, the imaging rays 13 to 15 respectively meet in one of the five image field points of the image field 9. The chief rays 13, which belong to each of the image field points, extend virtually parallel to one another. Thus, the imaging optical unit 7 according to FIG. 3 is virtually telecentric on the image side.

The imaging optical unit 7 has exactly four mirrors in the imaging beam path between the object field 6 and the image field 9, which mirrors are denoted by M1, M2, M3 and M4 in the sequence of their arrangement in the imaging beam path. The four mirrors M1 to M4 constitute for mutually separate optical components.

An aperture stop 17 is arranged in the beam path between the object field 6 and the mirror M1. The aperture stop 17 is arranged between the object field 6 and the mirror M1 in the region of a first pupil plane of the imaging optical unit 7 according to FIG. 3. A second pupil plane of the imaging optical unit 7 according to FIG. 3 lies between the mirror M2 and the mirror M3 in the imaging beam path 8.

The first mirror M1 in the beam path between the object field 6 and the image field 9 has an aspherical embodiment as a concave primary mirror, the second mirror M2 likewise has an aspherical embodiment as concave secondary mirror, the third mirror M3 has an aspherical embodiment as convex tertiary mirror and the fourth mirror M4 has an aspherical embodiment as concave quaternary mirror.

FIG. 3 depicts the curves of intersection of parent surfaces which are used for the mathematical modeling of the reflection surfaces of the mirrors M1 to M4. Those regions of the reflection surfaces of the mirrors M1 to M4 to which the coma rays 14, 15 are applied and between the coma rays 14, 15 imaging radiation is actually applied are actually physically present in the depicted sectional plane.

None of the mirrors M1 to M4 has a central passage opening for imaging light 4 to pass through. Depending on the operating mode, there may be partial obscuration of the imaging light 4 by edge regions of individual ones of the mirrors, for example by edge regions of the mirror M1.

An intermediate image 17a is situated in the imaging beam path between the mirrors M1 and M2.

The imaging optical unit 7 is designed for an operating wavelength of 13.5 nm.

The mirrors M1 to M4 bear a coating that is highly reflective to the illumination imaging light 4, which coating can be embodied as multilayer coating.

The mirror M4 is connected to a linear drive 18, which is depicted schematically in FIG. 3. With the aid of the linear drive 18, the mirror M4 can be displaced parallel to the z direction relative to the other three stationary mirrors M1 to M3 for changing a magnification value. The mirror M4, on the one hand, and one of the three other, non-displaceable mirrors M1 to M3, on the other hand, constitute two mirrors of the imaging optical unit 7, which can be displaced relative to one another for changing a magnification value. The mirror M4 is a zoom mirror. The setting of the mirror M4 according to FIG. 3 is also referred to as zoom setting Z1 in the following text.

Optical data of the imaging optical unit 7 according to FIGS. 3 and 4 will be reproduced below using two tables. In the column "radius", the first table shows in each case the radius of curvature of the mirrors M1 to M4. The third column (thickness) describes the distance in each case to the following surface in the z-direction. Here, the thickness value "thickness Z1" serves for the zoom setting Z1 according to FIG. 3.

The second table describes the exact aspherical surface form of the reflection surfaces of the mirrors M1 to M4, wherein the constant K and A to J are to be inserted into the following equation for the sag:

$$z(h) = \frac{ch^2}{1 + \text{SQRT}\{1 - (1+K)c^2h^2\}} + Ah^4 + Bh^6 + Ch^8 + Dh^{10} + Eh^{12} + Fh^{14} + Gh^{16} + Hh^{18}1 + Jh^{20}$$

Here, h represents the distance to the optical axis, i.e. to the normal 16, of the imaging optical unit 7. Thus, $h^2 = x^2 + y^2$ applies. The inverse of "radius" is inserted into the equation for c.

| Surface | Radius | Thickness Z1 | Thickness Z2 | Mode of operation |
|---|---|---|---|---|
| Object | Infinity | 263.181 | 263.181 | |
| Stop | Infinity | 436.819 | 436.819 | |
| M1 | −549.210 | −489.964 | −489.964 | REFL |
| M2 | 73.881 | 1189.297 | 1189.964 | REFL |
| M3 | 63.418 | −999.333 | −394.79 | REFL |
| M4 | 2424.319 | 1100.000 | 494.79 | REFL |
| Image | Infinity | 0.000 | 0.000 | |

| Surface | K | A | B | C | D |
|---|---|---|---|---|---|
| M1 | 0.000000E+00 | 4.579180E−11 | 2.024939E−16 | −2.550448E−21 | 1.034474E−25 |
| M2 | 0.000000E+00 | −6.023029E−08 | 1.502529E−10 | −1.277672E−12 | 6.306550E−15 |
| M3 | 0.000000E+00 | −8.705636E−07 | 1.460616E−08 | −7.500795E−10 | 2.646130E−11 |
| M4 | 0.000000E+00 | −2.002975E−11 | −3.678937E−16 | 3.387532E−20 | −1.329888E−24 |

| Surface | E | F | G | H | J |
|---|---|---|---|---|---|
| M1 | −2.133208E−30 | 2.694964E−35 | −1.874891E−40 | 5.554867E−46 | 0.000000E+00 |
| M2 | −1.921720E−17 | 3.537654E−20 | −3.610913E−23 | 1.572488E−26 | 0.000000E+00 |
| M3 | −5.751825E−13 | 7.268175E−15 | −4.894767E−17 | 1.359325E−19 | 0.000000E+00 |
| M4 | 2.169102E−29 | 0.000000E+00 | −2.919259E−39 | 8.384922E−45 | 0.000000E+00 |

An installation length T, i.e. a distance between the object plane 11 and the image plane 12 or the distance between the components of the imaging optical unit 7 spaced furthest apart in the z-direction is 1500 mm, depending on the embodiment of the imaging optical system. The distance between the object field 6 and the mirrors M1 to M4, i.e. the distance between the object field 6 and the closest mirror M2 is 210.036 mm. A ratio of installation length T and the magnification value 0 is 1500 mm/780=1.92 mm in the zoom setting Z1 according to FIG. 3.

The imaging optical unit 7 is a catoptric optical unit. The imaging optical unit 7 has exactly four mirrors M1 to M4. The imaging optical unit 7 is a coaxial system. An axis of rotational symmetry, in relation to which all four mirrors M1 to M4 are rotationally symmetric in relation to the embodiment of the reflection surface form thereof, extends along the z-direction, level with a y-coordinate between the object field 6 and the image field 9. The object field 6 is distanced from this axis of rotational symmetry in the direction of positive y-values. Due to the intermediate image 17*a*, the image field 9 is likewise distanced from this axis of rotational symmetry in the direction of positive y-values. Thus, in the projection optical unit 7, the fields 6, 9 lie off axis.

Figure 4:
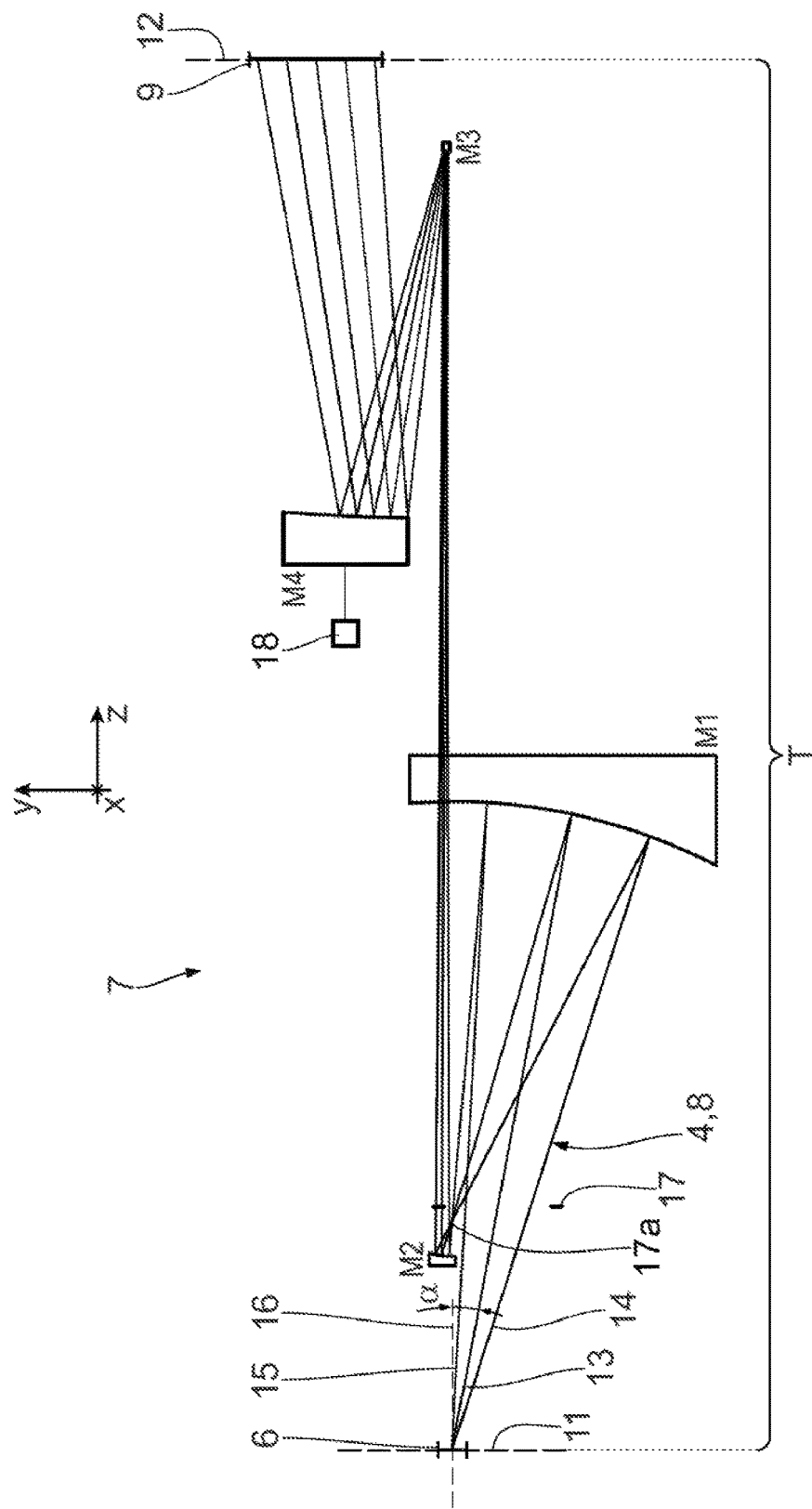
FIG. 4 shows the imaging optical unit according to FIG. 3 in a different zoom setting of exactly one displaceable mirror.

FIG. 4 shows the projection optical unit 7 in a second zoom setting Z2 of the mirrors M3 and M4. The position of the other mirrors M1 and M2 remains unchanged compared to the first zoom setting Z1. In the design tables above, the distance column "Thickness Z2" applies in relation to the zoom setting Z2.

Compared to the setting Z1, the mirror M4 is displaced by slightly more than 600 mm in the positive z-direction in the zoom setting Z2. Compared to the setting Z1, the mirror M3 is displaced in the z-direction by a few tenths of a millimeter in the zoom setting Z2.

In an alternative embodiment of a projection optical unit (not depicted here), which otherwise corresponds to the projection optical unit 7 according to FIGS. 3 and 4, it is only mirror M4 that is displaced between the zoom settings Z1 and Z2. In this alternative embodiment, the position of the other mirrors M1 to M3 remains unchanged compared to the first zoom setting Z1.

In the zoom setting Z2, the projection optical unit 7 according to FIGS. 3 and 4 has a magnifying magnification value of 487.500. In the zoom setting Z2, the object-side numerical aperture NAO is 0.125. The object field size is 244.8 µm in the y-direction and 326.4 µm in the x-direction. Thus, the object field 16 has a field size of 244.8×320 6.4 µm². The object field 16 continues to be rectangular.

Both the position and the size of the image field 9 are independent of the zoom setting of the projection optical unit 7.

In the following text, a further embodiment of an imaging optical unit 19 is described on the basis of FIGS. 5 and 6, which can be employed in place of the imaging optical unit 7 according to FIGS. 3 and 4. Components and functions corresponding to those which were already explained in the preceding figures are denoted by the same reference signs and will not once again be discussed in detail. The following text explains the differences to the preceding exemplary embodiment.

Figure 5:
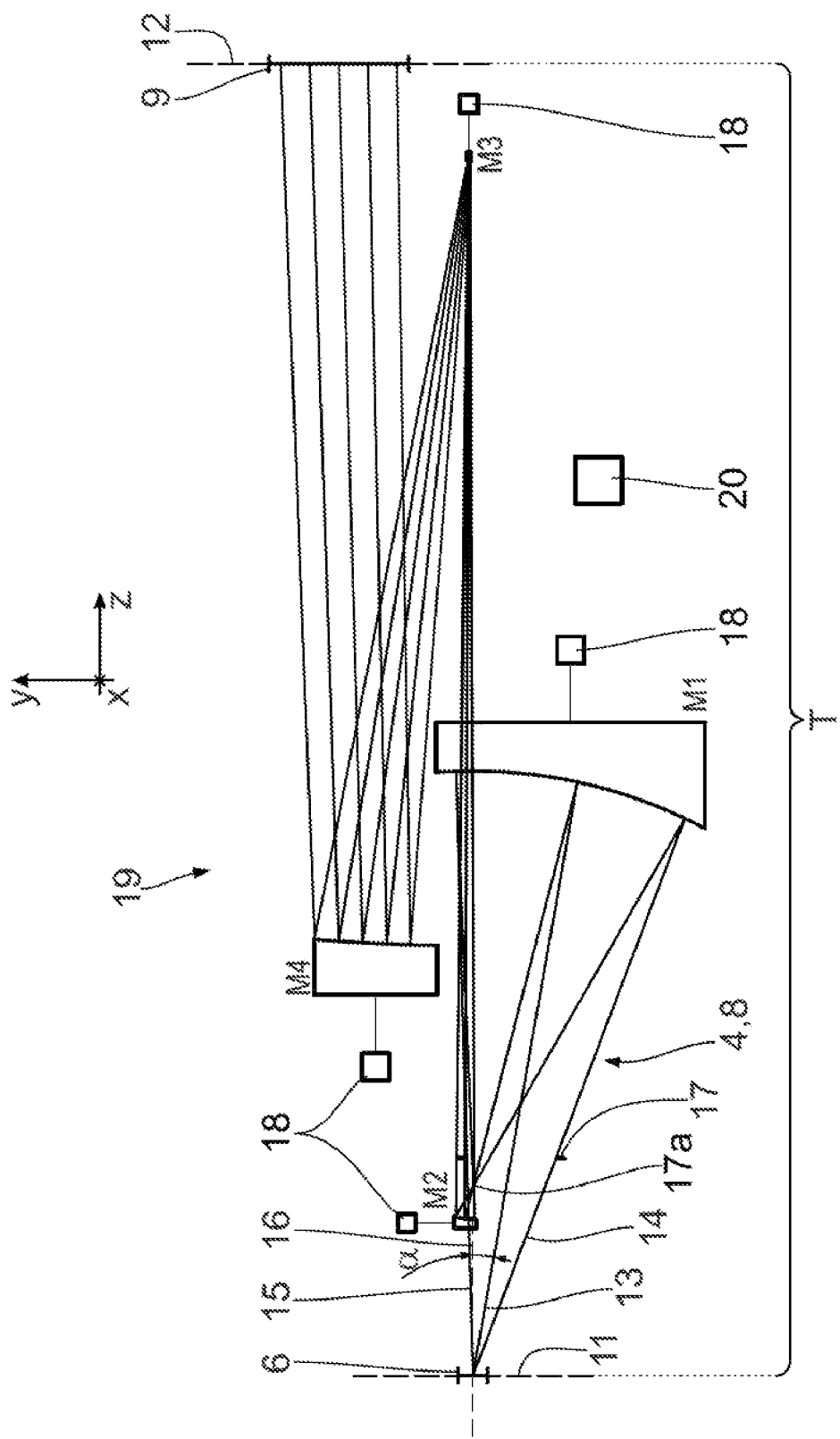
FIG. 5 shows a further embodiment of a magnifying imaging zoom optical unit, which can be used in place of the optical unit according to FIGS. 3 and 4.
Figure 6:
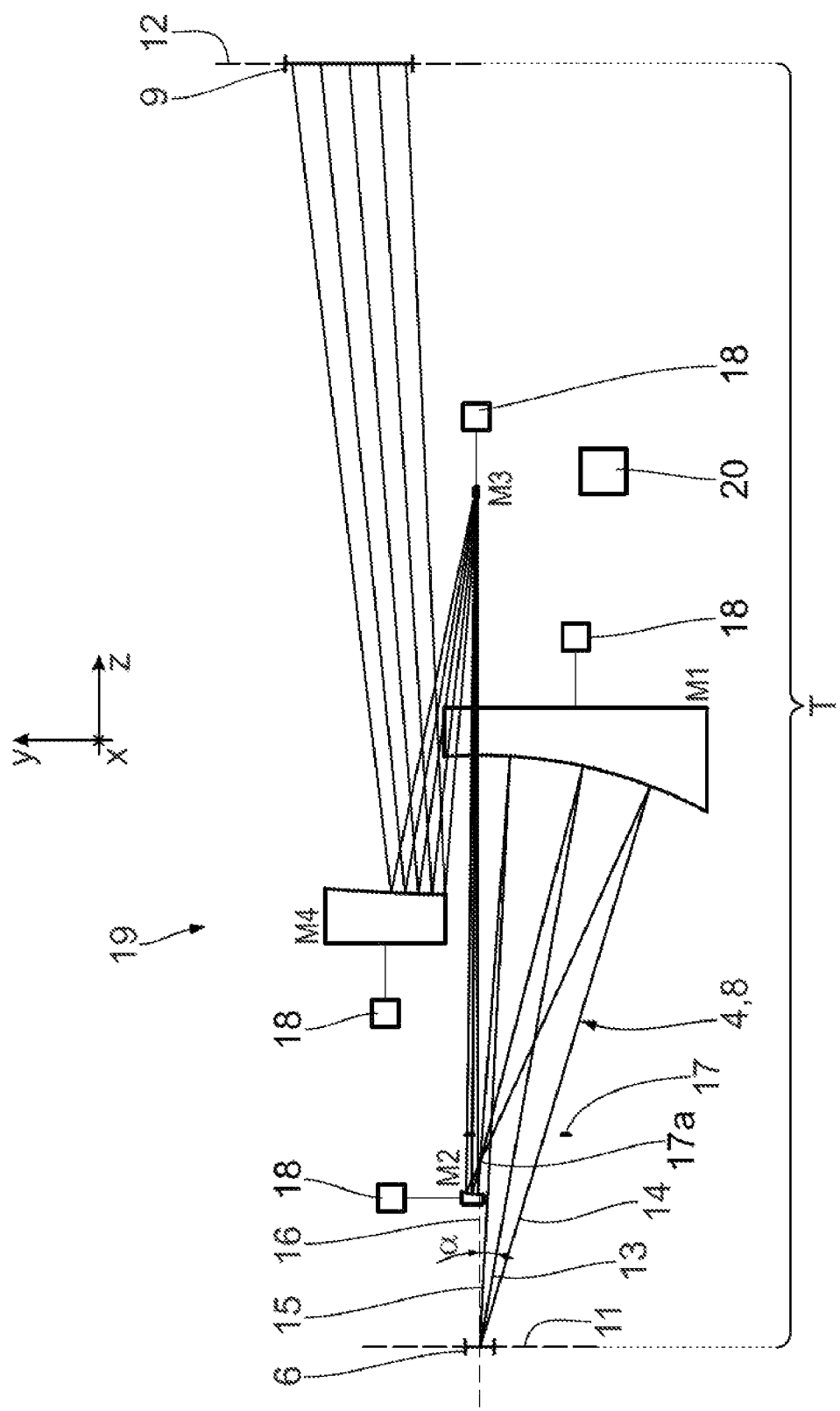
FIG. 6 shows the optical unit according to FIG. 5 in a different zoom setting of the mirrors of the imaging optical unit.

The imaging optical unit or projection optical unit 19 according to FIGS. 5 and 6 has exactly four mirrors M1 to M4.

In the projection optical unit 19 according to FIGS. 5 and 6, all mirrors are displaced for changing the magnification value between a magnifying magnification value of 780 in the zoom setting Z1 according to FIG. 5 and a magnifying magnification value of 487.5 in the zoom setting Z2 according to FIG. 6. Here, the mirror M1 is displaced by approximately 0.2 mm in the negative z-direction. Here, the mirror M2 is displaced by approximately 0.2 mm in the negative z-direction. The mirror M3 is displaced by approximately 350 mm in the negative z-direction. The mirror M4 is displaced by approximately 30 mm in the positive z-direction. The exact displacement values emerge from the distance values "Thickness Z2" in the following design tables.

All four mirrors M1 to M4 are each connected to respectively one linear drive 18. The four linear drives 18 are controlled by a common adaptive control 20, which is connected (not depicted here) to the four linear drives 18 of the embodiment according to FIGS. 5 and 6.

The position and the size of the image field 9 are also independent of the magnification value in the embodiment according to FIGS. 5 and 6.

Between the object plane 11 and the image plane 12, the imaging optical unit 19 has an installation length T of 1344 mm.

The ratio $T/\beta$ of installation length T and magnification value 0 ($\beta=780$) is $T/\beta=1.72$ in the zoom setting Z1 in the case of the imaging optical unit 19.

The optical data of the imaging optical unit 19 according to FIGS. 5 and 6 are reproduced below on the basis of two tables, the design of which correspond to the tables of the imaging optical unit 7 according to FIG. 3.

| Surface | Radius | Thickness Z1 | Thickness Z2 | Mode of operation |
|---|---|---|---|---|
| Object | Infinity | 222.512 | 222.512 | |
| Stop | Infinity | 397.079 | 397.249 | |
| M1 | −503.951 | −459.191 | −459.618 | REFL |
| M2 | 66.932 | 1083.863 | 729.991 | REFL |
| M3 | 57.504 | −803.931 | −416.456 | REFL |
| M4 | 2148.992 | 903.931 | 870.586 | REFL |
| Image | Infinity | 0.000 | 0.000 | |

| Surface | K | A | B | C | D |
|---|---|---|---|---|---|
| M1 | 0.000000E+00 | 4.822330E−11 | 1.610372E−16 | 9.196046E−21 | −6.950034E−25 |
| M2 | 0.000000E+00 | −4.843280E−08 | 1.030584E−10 | 1.297485E−12 | −2.487101E−14 |
| M3 | 0.000000E+00 | −1.246458E−05 | 1.667851E−06 | −1.139812E−07 | 4.166600E−09 |
| M4 | 0.000000E+00 | 2.716989E−09 | −7.316634E−13 | 1.159482E−16 | −1.130928E−20 |

| Surface | E | F | G | H | J |
|---|---|---|---|---|---|
| M1 | 2.964997E−29 | −7.093506E−34 | 9.230045E−39 | −5.543177E−44 | 8.163646E−50 |
| M2 | 1.725506E−16 | −5.966815E−19 | 9.536381E−22 | −3.098081E−25 | −5.419191E−28 |
| M3 | −6.984954E−11 | −2.283416E−13 | 3.014737E−14 | −4.720238E−16 | 2.507508E−18 |
| M4 | 6.990544E−25 | −2.748487E−29 | 6.664538E−34 | −9.090292E−39 | 5.337438E−44 |

The magnification value can be changed between a minimum magnification value, which is 487.5 in the embodiments according to FIGS. 3 to 6, and a maximum magnification value, which is 780. The distance between the object field 6 and the mirrors M1 to M4, i.e. the distance between the object field 6 and the closest mirror M2 is 160.400 mm.

The invention claimed is:

1. An imaging optical unit, comprising:
a first mirror; and
a second mirror,
wherein:
the first and second mirrors are displaceable relative to each other to change a magnification value of the imaging optical unit;
a size of an image field of the imaging optical unit is independent of the magnification value of the imaging optical unit;
a position of the image field of the imaging optical unit is independent of the magnification value of the imaging optical unit;
a distance between an object field of the imaging optical unit and the first mirror is finite; and
a distance between the object field of the imaging optical unit and the second mirror is finite.

2. The imaging optical unit of claim 1, wherein only one of the first and second mirrors is displaceable to change the magnification value of the imaging optical unit.

3. The imaging optical unit of claim 1, wherein each of the first and second mirrors is displaceable to change the magnification value of the imaging optical unit.

4. The imaging optical unit of claim 1, further comprising an aperture stop, wherein:
during use of the imaging optical unit, light passes along a path through the imaging optical unit from the object field to the image field; and
the aperture stop is in the path between the object field and the first mirror.

5. The imaging optical unit of claim 1, wherein:
during use of the imaging optical unit, light passes along a path through the imaging optical unit from the object field to the image field; and
the imaging optical unit has an intermediate image in the path between the first and second mirrors.

6. The imaging optical unit of claim 1, wherein the imaging optical unit is a catoptric imaging optical unit.

7. The imaging optical unit of claim 1, wherein no mirror of the imaging optical unit has a central passage opening configured to pass light during use of the imaging optical unit.

8. The imaging optical unit of claim 1, wherein:
the imaging optical unit has an object-side numerical aperture which is changeable between a minimum value and a maximum value by displacing the first and second mirrors relative to each other;
the minimum value of the object-side numerical aperture is 0.1; and
the maximum object-side numerical aperture is 0.25.

9. A system, comprising:
an imaging optical unit according claim 1; and
a spatially resolving detector configured to detect the image field,
wherein the system is an EUV mask inspection system.

10. An imaging optical unit, comprising:
at least two mirrors which are displaceable relative to each other to change a magnification value of the imaging optical unit,
wherein:
the magnification value of the imaging optical unit has a minimum value which is greater than 100; and
the magnification value of the imaging optical unit has a maximum value which is greater than 200.

11. The imaging optical unit of claim 10, wherein:
a size of an image field of the imaging optical unit is independent of the magnification value of the imaging optical unit;
a position of the image field of the imaging optical unit is independent of the magnification value of the imaging optical unit.

12. The imaging optical unit of claim 10, wherein only one of the first and second mirrors is displaceable to change the magnification value of the imaging optical unit.

13. The imaging optical unit of claim 10, wherein each of the first and second mirrors is displaceable to change the magnification value of the imaging optical unit.

14. The imaging optical unit of claim 10, further comprising an aperture stop, wherein:
during use of the imaging optical unit, light passes along a path through the imaging optical unit from the object field to the image field; and
the aperture stop is in the path between the object field and the first mirror.

15. The imaging optical unit of claim 10, wherein:
during use of the imaging optical unit, light passes along a path through the imaging optical unit from the object field to the image field; and
the imaging optical unit has an intermediate image in the path between the first and second mirrors.

16. The imaging optical unit of claim 10, wherein the imaging optical unit is a catoptric imaging optical unit.

17. The imaging optical unit of claim 10, wherein no mirror of the imaging optical unit has a central passage opening configured to pass light during use of the imaging optical unit.

18. The imaging optical unit of claim 10, wherein:
the imaging optical unit has an object-side numerical aperture which is changeable between a minimum value and a maximum value by displacing the first and second mirrors relative to each other;
the minimum value of the object-side numerical aperture is 0.1; and
the maximum object-side numerical aperture is 0.25.

19. The imaging optical unit of claim 10, wherein the imaging optical unit comprises precisely four mirrors.

20. A system, comprising:
an imaging optical unit according claim 10; and
a spatially resolving detector configured to detect the image field;
wherein the system is an EUV mask inspection system.

* * * * *

UNITED STATES PATENT AND TRADEMARK OFFICE
CERTIFICATE OF CORRECTION

PATENT NO. : 10,408,765 B2
APPLICATION NO. : 14/835308
DATED : September 10, 2019
INVENTOR(S) : Hans-Juergen Mann Page 1 of 1

It is certified that error appears in the above-identified patent and that said Letters Patent is hereby corrected as shown below:

In the Specification

Column 9, Line 11, delete "0" and insert -- β --, therefor.

In the Claims

Column 10, Line 55, Claim 9, after "according" insert -- to --.

Column 12, Line 20, Claim 20, after "according" insert -- to --.

Signed and Sealed this
Seventh Day of April, 2020

Andrei Iancu
*Director of the United States Patent and Trademark Office*